US005700693A

United States Patent [19]

Robins

[11] Patent Number: 5,700,693
[45] Date of Patent: Dec. 23, 1997

[54] METHOD TO DETECT BONE AND OTHER CONNECTIVE TISSUE DISORDERS IN HUMANS AND ANIMALS

[75] Inventor: Simon Peter Robins, Aberdeen, Scotland

[73] Assignee: The Rowett Research Institute, Aberdeen, Scotland

[21] Appl. No.: 471,364

[22] Filed: Jun. 6, 1995

Related U.S. Application Data

[63] Continuation of Ser. No. 41,761, Apr. 2, 1993, abandoned, which is a continuation of Ser. No. 633,379, Dec. 26, 1990, abandoned.

[30] Foreign Application Priority Data

Dec. 30, 1989 [GB] United Kingdom ............... 8929366

[51] Int. Cl.$^6$ ............................................ G01N 33/48
[52] U.S. Cl. ..................... 436/64; 435/7.92; 435/7.94; 435/7.23; 436/531; 436/86; 436/87; 436/161; 436/811; 436/813; 436/815
[58] Field of Search .................. 435/7.1, 7.9, 7.92, 435/7.23, 7.94, 70.21, 240.26, 240.27, 810, 975, 64; 436/512, 518, 530, 531, 548, 86, 87, 161, 811, 813, 815; 530/387.1, 387.9, 388.1, 389.1, 391.1, 391.5, 391.7

[56] References Cited

U.S. PATENT DOCUMENTS

| | | | |
|---|---|---|---|
| 4,973,666 | 11/1990 | Eyre | 530/323 |
| 5,140,103 | 8/1992 | Eyre | 530/327 |
| 5,283,197 | 2/1994 | Robins | 436/87 |

FOREIGN PATENT DOCUMENTS

| | | |
|---|---|---|
| WO89/04491 | 5/1989 | WIPO . |
| WO89/12824 | 12/1989 | WIPO . |

OTHER PUBLICATIONS

Black, D., et al., "Quantitative Analysis of the Pyridinium Crosslinks of Collagen in Urine Using Ion–Paired Reversed– Phase High–Performance Liquid Chromatography," *Anal. Biochem.* 169:197–203 (1988).
Black, D., et al., "Urinary Excretion of the Hydroxypyridinium Crosslinks of Collagen in Patients with Rheumatoid Arthritis," *Ann. Rheumat. Dis.* 48:641–644 (1989a).
Black, D., et al., "Excretion of Pyridinium Cross–Links in Ovariectomized Rats as Urinary Markers for Increased Bone Resorption," *Calcif. Tissue Int.* 44:343–347 (1989b).
Eyre, D., et al., "Identification of Urinary Peptides Derived from Crosslinking Sites in Bone Collagen in Paget's Disease," *J. Bone & Min. Res.* 3(1):s210, Abstract No. 565 (1988).
Eyre, D.R., et al., "Quantitation of Hydroxypyridinium Crosslinks in Collagen by High–Performance Liquid Chromatography," *Anal. Biochem.* 137:380–388 (1984).
Fujimoto, D., et al., "Isolation and Characterization of a Fluorescent Material in Bovine Achilles Tendon Collagen," *Biochem. & Biophys. Res. Commun.* 76(4):1124–1129 (1977).
Fujimoto, D., et al., "The Structure of Pyridinoline, a Collagen Crosslink," *Biochem. & Biophys. Res. Commun.* 84(1):52–57 (1978).
Fujimoto, D., and Moriguchi, T., "Pyridinoline, a Non–Reducible Crosslink of Collagen," *J. Biochem.* 83:863–867 (1978).
Fujimoto D., et al., "Analysis of Pyridinoline, a Cross–Linking Compound of Collagen Fibers, in Human Urine," *J. Biochem.* 94:1133–1136 (1983).
Gunja–Smith, Z., and Boucek, R.J., "Collagen Cross–Linking Compounds in Human Urine," *Biochem. J.* 197:759–762 (1981).
Macek, J., and Adam, M., "Determination of Collagen Degradation Products in Human Urine in Osteoarthrosis," *Z. Rheumatol.* 46:237–240 (1987).
Ogawa, T., et al., "A Novel Fluor in Insoluble Collagen: A Crosslinking Moiety in Collagen Molecule," *Biochem. & Biophys. Res. Commun.* 107(4):1252–1257 (1982).
Robins, S.P., "An Enzyme–Linked Immunoassay for the Collagen Cross–Link Pyridinoline," *Biochem. J.* 207:617–620 (1982).
Robins, S.P., "Turnover and Crosslinking of Collagen," in *Collagen in Health and Disease* (Weiss, J.B., et al., Eds.) Churchill Livingstone, Edinburgh, Scotland, pp. 160–178 (1982).
Robins, S.P., "Cross–Linking of Collagen," *Biochem. J.* 215:167–173 (1983).
Robins, S.P., and Duncan, A., "Cross–Linking of Collagen," *Biochim. J.* 215:175–182 (1983).
Robins, S.P., et al., "Measurement of the Cross Linking Compound, Pyridinoline, in Urine as an Index of Collagen Degradation in Joint Disease," *Ann. Rheumat. Dis.* 45:969–973 (1986).
Robins, S.P., and Duncan, A., "Pyridinium Crosslinks of Bone Collagen and Their Location in Peptides Isolated from Rat Femur," *Biochem. et Physiophys. Acta* 914:233–239 (1987).
Robins, S.P., et al., "Urinary Hydroxy–Pyridinium Crosslinks of Collagen as markers of Resorption in a Range of Metabolic Diseases," *J. Mineral & Bone Res.* 4:s397 (1989).
Seibel, M.J., et al., "Urinary Hydroxy–Pyridinium Crosslinks Provide Indices of Cartilage and Bone Involvement in Arthritic Diseases," *J. Rheumatol.* 16(7):964–970 (1989).
Wu, J.–J., and Eyre, D.R., "Identification of Hydroxypyridinium Cross–Linking Sites in Type II Collagen of Bovine Articular Cartilage," *Biochemistry* 23:1850–1857 (1984).

*Primary Examiner*—Susan Wolski
*Attorney, Agent, or Firm*—Peter J. Dehlinger; Vincent M. Powers

[57] ABSTRACT

The invention is directed to methods to assess connective tissue, especially bone, metabolism in disease or to monitor therapy, which method comprises assessing the levels of native free collagen-derived crosslinks in biological fluids, especially urine. The method can be enhanced by concomitantly determining the levels of an indicator of bone formation in biological fluids of the same individual and assessing the differences between the degradation marker and the formation indicator. Antibodies which are specifically immunoreactive with forms of crosslinks which occur free in biological fluids are also disclosed.

13 Claims, 1 Drawing Sheet

METHOD TO DETECT BONE AND OTHER CONNECTIVE TISSUE DISORDERS IN HUMANS AND ANIMALS

This is a continuation of application Ser. No. 08/041,761, filed Apr. 2, 1993, abandoned, which is a continuation of application Ser. No. 07/633,379, filed Dec. 26, 1990, abandoned.

TECHNICAL FIELD

The invention relates to methods of diagnosis in medical and veterinary contexts. More specifically, it concerns methods to assess bone and other connective tissue metabolism by detecting free crosslinks formed by collagen degradation in biological fluids, such as urine.

BACKGROUND ART

The association of collagen as a major structural material in a multiplicity of tissues, including bone, cartilage, skin, tendons, dentine and various soft tissues is well known. It is also known that the fiber structure of collagen is stabilized by crosslinking. The presence of the fluorescent pyridinium ring system as a non-reducible crosslink in collagen was reported by Fujimoto, D., et al., *J Biochem* (1978) 83:863–867. The Fujimoto paper reported isolation of a fluorescent peptide from pronase digestion of bovine Achilles tendon collagen. The isolated hydrolyzed pyridinoline (Pyd) was thought to contain three residues of hydroxylysine and it was recognized that, prior to hydrolysis, peptide fragments were attached to the pyridinoline moiety. Further work on characterization was conducted by Gunja-Smith, Z., et al., *Biochem J* (1981) 197:759–762, using hydrolyzed urine, and advantage was taken of the presence of the pyridinoline in urine by Robins, S. P., *Biochem J* (1982) 207:617–620, who linked pyridinoline obtained from hydrolyzed urine to a carrier to raise antibodies. The antibodies were then employed in an immunoassay to determine the concentration of pyridinoline in hydrolyzed urine. The procedure was stated by Robins as useful to provide an index of the degradation of certain forms of mature collagen by analysis of physiological fluids.

In all of the foregoing, hydrolyzates were employed to obtain total pyridinoline since much of the crosslink retained peptide extensions of the hydroxylysyl residues responsible for its formation. Thus, in order to obtain a homogenous preparation containing the pyridinium ring, a preliminary hydrolysis step was necessary.

By 1982, it was established that there were two pathways of crosslink formation depending on whether lysine or hydroxylysine residues were present in the telopeptides from which these crosslinks were derived (Robins, S. P., in "Collagen in Health and Disease" (1982) Weiss, J. B., et al., eds., pages 160–178, Churchill Livingstone, Edinburgh). This was stated to result in a specificity of crosslinking whereby in soft tissues, such as skin, reducible aldimine linkages are formed from oxidized lysyl residues, whereas in cartilage and bone these bonds, initially formed from hydroxylysine aldehydes, undergo a spontaneous rearrangement to more stable oxoimine crosslinks. These bonds undergo further reaction to form 3-hydroxy-pyridinium crosslinks. The stable crosslinking pyridinoline analog involving lysine rather than hydroxylysine in the helix portion was identified and quantified by Ogawa, T., et al., *Biochem Biophys Res Commune* (1982) 107:1251–1257; Eyre, D. R., et al., *Anal Biochem* (1984) 137:380–388, and designated deoxypyridinoline (Dpd). This material was then believed to be restricted to bone collagen, although amounts vary between species.

Further work by Robins, S. P., *Biochem J* (1983) 215:167–173, provided evidence for the existence of glycosylated pyridinoline in bone. Robins proposed a structure which showed the derivation of the ring from three residues of hydroxylysine and also showed that alkali hydrolyzates of collagen provided an O-galactosyl derivative substituted at the sidechain hydroxy group. As this material was extremely labile to mild acid treatment, this material would not have been present in samples of hydrolyzed tissue or body fluid.

Fujimoto, D., et al., *J Biochem* (1983) 94:1133–1136, chromatographed unhydrolyzed urine samples and showed that the 3-hydroxypyridinium ring portion was present in substantial proportion as the "free" form, i.e., the three hydroxylysyl-derived residues which composed it did not contain further peptide extensions. On amino acid analysis, whereas pyridinoline isolated from an acid hydrolyzate of collagen gave an asymmetric peak, "free" urinary pyridinoline gave a symmetric peak. The authors concluded this to be due to isomerization by epimerization of the hydroxylysine moiety of the pyridinoline system during hydrolysis. In addition, relationship of levels of total pyridinoline (after hydrolysis) to age was determined by these workers as a ratio to creatinine levels. It was found that the ratio was high in the urine of children but decreased with age until growth ceases. It was further found that this ratio is relatively constant in adults, but increases slightly in old age. The authors speculate that this may correspond to the loss of bone mass observed in old age.

Attempts were also made to characterize the above-mentioned peptide extensions. Robins, S. P., et al., *Biochem J* (1983) 215:175–182, proposed that in cartilage-derived type II collagen, the pyridinoline links two C-terminal telopeptide chains with a single chain of the helical peptide. An additional pyridinoline crosslink, i.e., with the ring derivatized to other peptides, was thought to link two N-terminal non-helical peptides with a third chain in the helical portion of the molecule. The studies were conducted by isolating the fluorescent pyridinoline crosslinks from tissues by specific cleavage with CNBr, thus preserving peptide sequences as extensions of the hydroxylysyl residues forming the ring. The crosslink was localized in the collagen fibers by determining the amino acid sequences of these extensions.

In a paper similar in approach to that of Robins (supra), Wu, J. J., et al., *Biochemistry* (1984) 23:1850–1857, conducted CNBr cleavage of mature cartilage and determined the sequence of the peptide extension residues of the hydroxylysyl participants in the pyridinium ring. Their conclusions were similar to those of Robins.

Robins, S. P., et al., *Biochim Biophys Acta* (1987) 914:233–239, used CNBr digestion of bone derived collagen to localize the crosslinks in the type I collagen structure. These authors concluded that the proportions of the crosslink derived from lysine and that derived from hydroxylysine were present in the same proportions in each of the isolated peptide forms. They also concluded that this showed that these two crosslink analogs occupy the same loci in the collagen fiber and that the form apparently derived from one lysyl participant appears to arise through incomplete hydroxylation of the appropriate lysine residues in the helix. Amino acid analysis indicated that the crosslinks must be situated at two locations involving both the N- and C- terminal telopeptide regions.

Henkel, W., et al., *Eur J Biochem* (1987) 165:427–436, determined the amino acid sequences associated with the crosslinks in type I collagen isolated from aorta. These sequences are different from those obtained for type II collagen. Similar results were found by Eyre, D. R., et al., *FEBS* (1987) 2:337–341, who demonstrated that the crosslinks from type IX and type II collagens displayed distinctive peptides attached to the pyridinoline crosslinks.

PCT application WO89/04491 to Washington Research Foundation proposes a urinary assay for measuring bone resorption by detection in urine of the specific crosslinks, characterized by their peptide extensions, associated with bone collagen. The assay relies on quantifying the concentration of peptides in a body fluid where the peptide fragments having a pyridinium crosslink are derived from bone collagen resorption. Two specific entities having peptide extensions presumed to be associated with bone collagen are described. These are obtained from the urine of patients suffering from Paget's disease, a disease known to involve high rates of bone formation and destruction.

Macek, J., et al., *Z Rheumatol* (1987) 46:237–240, proposed an assay for osteoarthrosis which depends upon the peptides associated with the crosslinks from collagen breakdown. In this approach, the urine sample was size-separated for peptides of molecular weight greater than 10 kd, which peptides were then separated by HPLC using a fluorescence detector to determine those fractions containing the fluorescence due to the pyridinium ring. The spectra obtained from patients with osteoarthrosis were compared to those from healthy patients, and it was easily demonstrable that the multitude of fluorescent peaks associated with the diseased condition was absent from the healthy counterpart. Furthermore, urine from the same diseased patient two weeks after total endoprosthesis of the diseased hip, thereby decreasing the products of osteoarthrosis, gave a spectrum of fluorescent peaks which more closely resembled that of normals. Furthermore, the osteoarthrosis spectrum was readily distinguished from that obtained from patients with rheumatoid arthritis. The closer resemblance of the rheumatoid arthritis spectrum to that of the spectrum from normal controls was attributed by the authors to the higher activity of proteases in rheumatoid arthritis. This was presumed to digest collagen structures into smaller fragments not detectable in their system.

Study of the elevated levels of total 3-hydroxypyridinium ring crosslinks in hydrolyzed urine of patients with rheumatoid arthritis has also been suggested as a method to diagnose this disease by Black, D., et al., *Annals of Rheumatic Diseases* (1989) 48:641–644. The levels of "hydrolyzed" crosslink for patients with rheumatoid arthritis (expressed as a ratio of this compound to creatinine) were elevated by a factor of 5 as compared to controls. In this method, crosslinks derived from hydroxylysine were distinguishable from those derived from lysine; only the hydroxylysine-derived crosslinks were measurably increased. In a more extensive study using hydrolyzed urines, Seibel et al., *J. Rheumatol* (1989 16:964–970, showed significant increases in the excretion of bone-specific crosslinks relative to controls in both rheumatoid and osteoarthritis, but the most marked increases for hydroxylysine-derived pyridinium were in patients with rheumatoid arthritis.

While measures related to the presence of collagen-derived crosslinks have been used as indices of the degradation of specific collagen types, including that of bone, conversely, efforts have been made to identify markers of bone formation. Delmas, P. D., et al., *J Bone Mineral Res* (1986) 1:333–337, used the level of GLA- protein in serum as a marker for bone formation in children; the same group, Brown, J. P., et al., used a similar assay to assess bone formation in post-menopausal osteoporosis (*Lancet* (1984) 1091–1093.

There are many conditions in humans and animals which are characterized by a high level of bone resorption and by an abnormal balance between bone formation and bone resorption. Among the best known of these are osteoporosis and Paget's disease. However, abnormalities in bone metabolism occur in a variety of other conditions including the progress of benign and malignant tumors of the bone and metastatic cancers which have been transferred to bone cells from, for example, prostate or breast initial tumors. Other conditions include osteopetrosis, osteomalacial diseases, rickets, abnormal growth in children, renal osteodystrophy, and a drug-induced osteopenia. Irregularities in bone metabolism are also often side effects of thyroid treatments and thyroid conditions per se, such as primary hypothyroidism and thyrotoxicosis as well as Cushing's disease. It would be useful to have a diagnostic which readily recognizes a subject's condition as an irregularity in bone metabolism, even without defining the precise syndrome from among the possible choices, such as those listed here. Additional tests within the sphere of known bone diseases can be performed once it is established that this is the subset of problems from which diagnosis will emerge.

The invention provides just such a screening test, which is general for bone metabolism abnormalities.

DISCLOSURE OF THE INVENTION

The invention provides a straightforward, and noninvasive, if desired, test to identify subjects who have conditions which are characterized by abnormalities in the formation and resorption of bone and the balance between them. The test is based on the quantitation of native free pyridinoline or deoxypyridinoline crosslinks derived from collagen degradation which are present in biological fluids such as serum and urine. The test is specifically directed to either or both of the forms of crosslinks which occur in such fluids in forms independent of additional amino acid sequence associated with the condensed lysyl or hydroxylysyl residues which constitute the collagen-derived crosslinks.

Accordingly, in one aspect, the invention is directed to a method to diagnose the presence of disorders associated with bone metabolism abnormalities, which method comprises assessing the level of native free crosslinks in a biological fluid of the subject. This level is then compared with the level of the native free crosslinks in normal subjects. Elevated levels of native free crosslinks indicate the presence of such abnormalities.

This method can be fine-tuned by assessing the level of these degradation products in comparison with indicators of bone formation. Additional information as to the condition of the subject can be obtained if it is found that the difference between the level of bone resorption, as characterized by the presence of native free crosslinks in the biological fluid, and the level of bone formation, as characterized by the level of the indicator, is the same or different from that of normal subjects. In general, those suffering from disorders which deplete the skeletal structure are characterized by larger differences between the resorption and formation rates, where resorption predominates.

Thus, a further aspect of the invention is directed to a method to diagnose the presence of the above-mentioned metabolism abnormalities which comprises comparing the levels of an indicator of bone formation in a biological fluid with the level of native free crosslinks in a biological fluid from the same individual and comparing the difference between these levels and the differences found for normal subjects. Elevated differences between bone resorption and bone formation indicate problems in maintaining skeletal integrity.

It has been found by the inventor herein that antibodies which bind to hydrolyzed free crosslinks obtained from tissues or biological fluids by treatment with acids are not cross-reactive with native free crosslinks—either those which contain a lysyl sidechain or those with a hydroxylysyl sidechain. However, antibodies may be prepared which are specific for these free crosslinks. These antibodies may not be cross-reactive with the hydrolyzed forms; for purposes of assessing biological samples directly, this does not matter, as the hydrolyzed forms are not present. These antibodies may be prepared, if desired, so as to distinguish between the lysyl and hydroxylysyl sidechain-containing native free crosslink forms. Based on previous experience with polyclonal antibodies against hydrolyzed pyridinoline, the antibodies are likely to distinguish the free forms from the native peptide-containing forms.

Accordingly, another aspect of the invention is directed to antibodies specifically immunoreactive with the native free crosslinks or with either the lysyl or hydroxylysyl forms of native free crosslinks, or with the glycosylated forms thereof.

Another aspect of the invention is a method to identify subsets of arthritic disease by determining the breakdown of other connective tissues, including cartilage, which method comprises determining the ratio of hydroxylysyl sidechain crosslinks to lysyl sidechain crosslinks (Pyd/Dpd) in a biological fluid of a subject and comparing said ratio to that in normal controls, wherein an increase in said ratio in said subjects over normal controls indicates cartilage breakdown in said subject.

Another aspect is a method of determining the presence of an indicator of connective tissue formation which, in combination with free crosslink levels, provides an assessment of the subject's metabolic state.

Still another aspect provides a kit for immunoassay determination of the amount or concentration of native free crosslinks in a biological fluid, said crosslinks being determinable as total free crosslinks or those selected from the group consisting of Pyd, Dpd, Gal-Pyd and Glc. Gal-Pyd. The kit includes a set of containers at least one of which contains an antibody composition specifically immunoreactive with native free total crosslinks, or one or more of Pyd, Dpd, Gal-Pyd or Glc. Gal-Pyd, and at least one of which contains an additional reagent for conduct of the immunoassay such as a label along with instructions for the conduct of the assay. Preferably, the biological fluid is a serum or urine. The free crosslinks may then be determined as total native free crosslinks. However, the free crosslinks can be determined individually as lysyl sidechain crosslinks (Dpd) or as hydroxylysyl sidechain crosslinks (Pyd), or as glycosylated Pyd, or any combination of these.

In still another aspect, the invention is directed to the use of the assay kits containing the antibodies of the invention or fragments thereof as specific reagents for the crosslinks to be detected.

MODES FOR CARRYING OUT THE INVENTION

The invention provides an improvement over the presently available methods to diagnose bone disorders or other diseases characterized by abnormalities in collagen metabolism. The invention method utilizes variations in the levels of collagen-derived pyridinium crosslinks in biological fluid as an index of these abnormalities. Prior art methods have involved the hydrolysis of a sample, typically urine, to provide analyte in the form of hydrolyzed crosslinks, free of peptide sidechains, which can then be quantitated in an immunoassay using antibodies raised with respect to the hydrolyzed crosslinks. While this method provides useful information, the preliminary hydrolysis required prevents the assay from becoming a simple clinical assay run directly on an untreated biological sample.

It has been found, by the inventors herein, that antibodies raised with respect to the hydrolyzed forms of the pyridinium crosslink do not cross-react either with the free crosslinks present in urine or other biological fluids, or with these crosslinks conjugated to peptides prior to hydrolysis. Thus, the antibodies presently available in the art cannot be used directly with an untreated biological sample.

The present invention overcomes this disadvantage by providing reagents which can be reacted directly with the biological sample to determine the crosslinks present in free form as the diastereomer present prior to hydrolysis. As shown in the examples below, direct measurement of these free and unhydrolyzed crosslinks provides data which are comparable to those obtainable only through the presently available, more complex assay.

Some background information as to the crosslink structures involved will be useful:

Nature of the Crosslinks

The abbreviations Dpd and Pyd will be used herein to denote the two known forms of the isolated crosslink itself. Pyd or pyridinoline refers to crosslinks formed wherein the ring N is the ε amino of a hydroxylysyl residue; Dpd or deoxypyridinoline refers to crosslinks formed wherein the ring N is ε amino of a lysyl residue. (Various methods of denoting these variations have been used; for example, HP has been used to designate the "hydroxylysyl" form, and LP has been used to refer to the "lysyl" form.)

Specifically, Dpd is believed to represent compounds of the formula:

and Pyd is believed to describe compounds of the formula:

It is seen that both forms of crosslinks are 1,4,5 trisubstituted 3-hydroxypyridinium residues. Pyd has a free hydroxyl group on the sidechain which can be glycosylated, and it is known to be glycosylated in some tissues. The glycosylation is labile to acid, and also to base, but to a lesser degree. Pyd has been shown to occur as Gal-Pyd; the inventor herein has also demonstrated the presence of Glc. Gal-Pyd in urine (see PCT application WO 89/00715). These forms of free Pyd have the acetals conjugated to the sidechain hydroxyl, respectively.

It is seen that Dpd contains three chiral centers—those of the three α-amino positions in the sidechains. Pyd contains four such centers, as there is an additional chiral center at the sidechain hydroxyl position. Presumably, in the unhydrolyzed samples, whether derivatized further to peptides or not, the three α-amino groups are derived from the natively occurring L-enantiomers, and the OH is in a configuration also determined by the biological system.

As set forth in the Background section above, a substantial proportion of the crosslinks present in urine (about 40% in adults) is in the form of "free" crosslinks—i.e., there are no peptide chains conjugated to the Pyd, glycosylated Pyd, or Dpd structures shown above, even before hydrolysis of the sample is conducted. Thus, by "free" crosslink is meant compounds of the formulas shown above.

It is noted that with respect to Pyd and Dpd, the chirality of the chiral centers is not specified. Thus, "free," refers to these crosslinks, whether or not they have been subjected to hydrolysis conditions. The present work demonstrates that these "free" crosslinks differ in chirality when obtained in their "native" form, as compared to their "hydrolyzed" form. As used herein, "native free" crosslinks refers to Dpd or Pyd or its glycosylated forms as they occur in free form in the biological sample; "hydrolyzed free" crosslinks refers to these structures as they occur in hydrolysates. Of course, as the glycosidic bond is labile to the hydrolysis conditions, "hydrolyzed free" crosslinks will not contain sugars.

Figure 1:
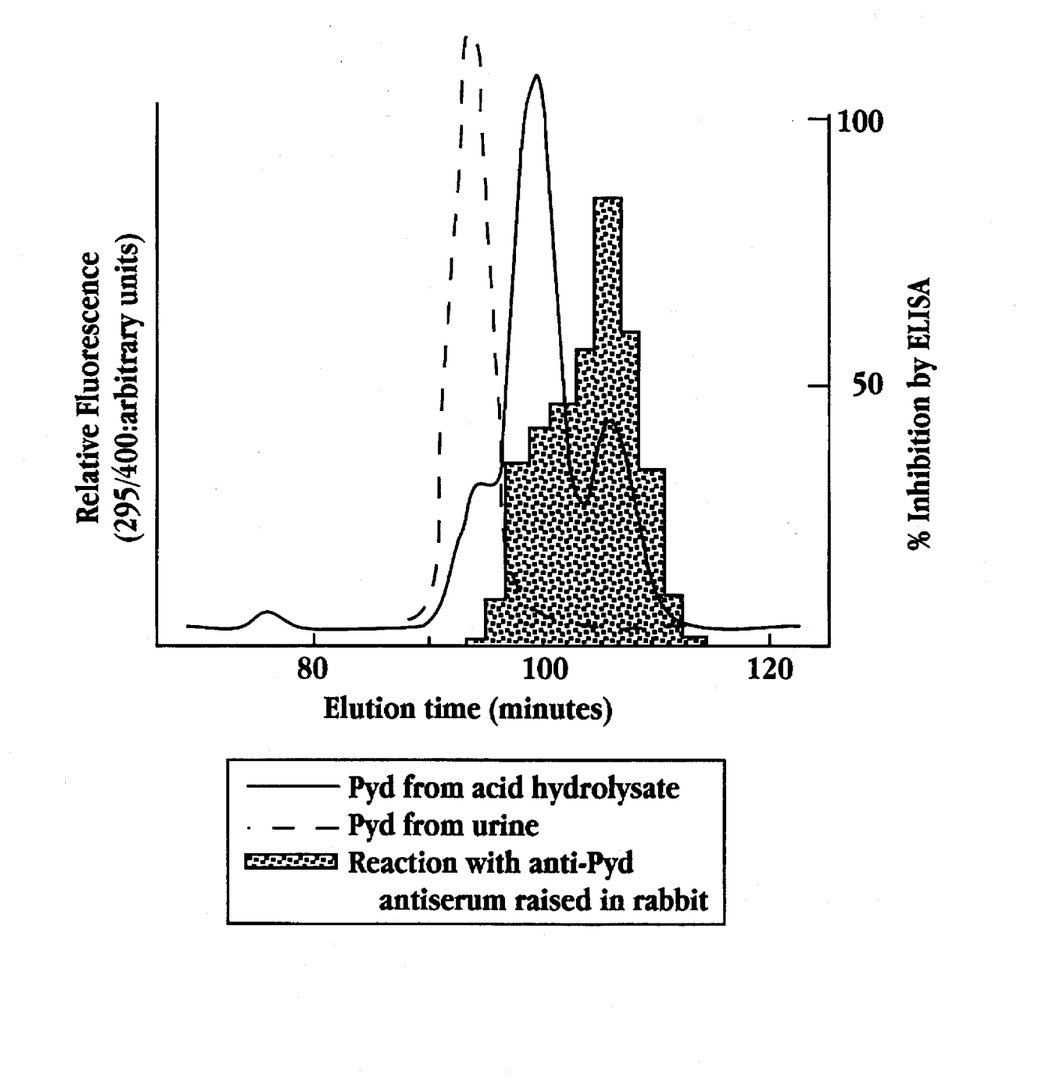
FIG. 1 shows a chromatographic trace of pyridinoline obtained from an acid hydrolyzate superimposed on a trace of the pyridinoline obtained without hydrolysis from urine. The figure further compares the elution pattern as determined by fluorescence with the elution pattern as determined by reaction with anti-pyridinoline antibody prepared from hydrolyzate.

As the native free crosslinks are the product of the biological system, it is assumed that the biologically favored chirality occurs at all three or four chiral centers. Presumably the three chiral centers represented by the α-amino groups of the sidechains are in the L configuration, as in the naturally occurring amino acid, and the chirality of the carbon containing the sidechain hydroxyl in Pyd is also representative of a single configuration. This is confirmed by the results shown in FIG. 1, in which the dotted line represents the result of ion-exchange chromatography on sulfonated polystyrene beads (7 μ) equilibrated with sodium citrate performed with the previously isolated Pyd in its native free form. As seen in FIG. 1, the Pyd isolated directly from urine elutes at a single peak. This is consistent with the presence of only a single diastereomer.

After hydrolysis, however, the hydrolyzed free Pyd elutes as a mixture, shown by the solid line in FIG. 1. This is consistent with racemization at the chiral centers to obtain a mixture of diastereomers which no longer exhibit identical chromatographic behavior. Similar results are obtained comparing native free Dpd with hydrolyzed free Dpd.

The "native free" crosslinks thus differ from hydrolyzed free forms of crosslinks, It appears that during conventional acid hydrolysis racemization occurs which changes the configuration of some of the molecules. However, enhancement of the yield of total "native free" crosslinks in the biological sample could also be obtained by proteolytic treatment of total native Dpd and Pyd to liberate the "native free" crosslink form. In addition, the crosslinks per se are identical across species, and other species besides human could be utilized to prepare native free crosslink standards for use in the assay system or for use as immunogens. In particular, porcine urine contains high amounts of native free crosslinks. Any source of the biologically important diastereomer could be used.

It has been shown by the inventor herein that the antibodies raised against the free Pyd which is generated as the result of hydrolysis—i.e., wherein the immunogen is obtained by treating the biological fluid or tissue in concentrated acid so as to destroy peptide linkages and separating Pyd from Dpd—show little or no cross-reactivity with native free forms of either Dpd or Pyd. Furthermore, antibodies raised against the Pyd formed from the hydrolyzate cross-react only slightly with Dpd thus formed. Antibodies raised against Pyd from an acid hydrolyzate of bone or cartilage do cross-react with the crosslink in urine after acid hydrolysis.

A typical set of results is shown in Table 1. Table 1 presents the results of an ELISA assay using antiserum obtained by immunization with the Pyd hydrolyzate isolated from bone. The ELISA uses this hydrolyzate as antigen, and the results are given in terms of the ability of the candidate crosslink to inhibit the binding of the hydrolyzate antigen to the antiserum. Using this criterion, antibodies which were obtained by immunization of rabbits against Pyd isolated from an acid hydrolyzate of cartilage or bone were only 5% cross-reactive with Pyd in its native free form from urine (U-Pyd) although completely cross-reactive with Pyd after hydrolysis in acid of the purified native, free crosslink isolated from urine. These antibodies, further, were 20% cross-reactive with Dpd isolated from the same bone hydrolyzate and were less than 1% cross-reactive with Dpd in its native free form from urine (U-Dpd); about 70% of the reactivity with these antibodies was recovered after acid hydrolysis of the native free form (Table 1).

TABLE 1

| | pmol required for 50% inhibition | % Cross reaction |
|---|---|---|
| Pyd from hydrolyzate of bone | 1.6 | 100 |
| Free Pyd from urine (U-Pyd) | 29.6 | 5 |
| U-Pyd from urine hydrolyzed in acid | 1.5 | 107 |
| Dpd from hydrolyzate of bone | 8.1 | 20 |
| Free Dpd from urine (U-Dpd) | >260 | <1 |
| U-Dpd from urine hydrolyzed in acid | 11.5 | 14 |

This is further shown in FIG. 1, which, as stated above, presents the result of ion-exchange chromatography on sulfonated polystyrene beads (7 µ) equilibrated with sodium citrate. The elution patterns for the free Pyd and the acid hydrolyzate of urine were determined by fluorescence. Antibodies raised against the acid hydrolyzate are shown to react significantly only with the hydrolyzate. The discrepancy in reactivity of the two major hydrolyzate peaks is attributable to the differing immunogenicity of these two fractions.

Preparation of Antibodies to Native Free Crosslinks

Antibodies are prepared to the native free crosslink either as a total fraction or, preferably, to each component of this fraction. Gross separation of the pyridinium linkage in its "free" forms from the fragments containing protein can be achieved, for example, by the method of Fujimoto, D., *J Biochem* (1983) 94:1133–1136 (supra). In this preparation, a concentrate of urine is applied to a Sephadex G-10 column and the total pyridinium-containing fractions eluted. The eluate is then applied to a column of phosphocellulose equilibrated with sodium citrate, and eluted with salt. This rather simple procedure results in the "free" crosslinks as a single peak. As the sample is not subjected to hydrolysis conditions this peak contains not only the Dpd and Pyd forms, but also glycosylated Pyd including Gal-Pyd and Glc. Gal-Pyd as described above. Further separation of this native free crosslink fraction is then conveniently conducted by standard methods, for example using ion exchange on sulfonated polystyrene beads as described above, or using HPLC. Typical protocols for this separation are found, for example, in Black, D., et al., *Anal Biochem* (1988) 169:197–203; Seibel, M. J., et al., *J Rheumatol* (1989) 16:964–970.

Antibody preparation is by conventional techniques including injection of the mixture or the individual components conjugated to carrier into suitable mammalian subjects such as rabbits or mice according to immunological protocols generally known in the art. The materials are conjugated to carriers such as BSA or tetanus toxoid using standard conjugation methods to enhance immunogenicity. Sera are titrated to determine antibody formation with respect to the immunogen. If desired, spleen cell or peripheral blood lymphocytes may be harvested and immortalized to produce cultures of cells capable of continuous production of monoclonal antibodies immunoreactive with the desired component. These preparations have enhanced specificity with respect to the individual components.

Thus, polyclonal antisera can be obtained which are specifically immunoreactive with the native free form of the crosslinks occurring in biological fluids, in particular in urine. By "specifically immunoreactive" is meant that the serum is capable of forming complexes with the native free crosslink forms in the biological fluid with sufficiently greater affinity in comparison to other materials in the fluid to permit determination of the native free forms in an immunoassay. Some portion of the polyclonal antiserum prepared either with respect to the mixture of native free forms or with respect to the individual components may crossreact with the native forms having peptide chains attached; assays can be standardized either by preparation of monoclonal antibodies which do not thus crossreact, or by standardizing to account for this crossreactivity.

The availability of routine techniques to obtain monoclonal antibody preparations permits reproducible reproduction of antibodies of the desired specificity. Thus, by utilizing a screening procedure which utilizes as a criterion the ability of the immortalized cell supernatant to immunoreact with, for example, native free Pyd, but to fail to react either with native free Dpd or forms of the crosslinks which are further conjugated to peptides, a reliable source of antibodies which react only with native free Pyd can be obtained. Conversely, it may be advantageous to use, in assessment of biological samples, cocktails of antibodies with these unique specificities so that all native free forms are determined.

Immortalized cell lines which secrete antibodies of the desired specificity can be cultured in vitro for the production of practical quantities of the desired monoclonals using mammalian cell techniques known in the art. Such culture techniques are now available on a commercial scale. In addition, the immortalized cell lines may be injected into mice and a somewhat cruder preparation of the monoclonals isolated as the ascites fluid. The antibody preparation may also be affinity purified if desired using the immunogen as an affinity ligand.

It should be noted that while it is clear that antibodies prepared with respect to the hydrolyzed free forms of the collagen-derived crosslinks failed to react with the native free forms, it is not of importance whether the converse is true, since hydrolyzed forms are not present in unhydrolyzed biological samples. Thus, screening procedures to assure the absence of this cross-reactivity are unnecessary.

Conduct of Immunoassays

Accordingly, by utilization of an immunoassay with the antibodies prepared as above it is possible to assay a biological fluid sample without prior fractionation or hydrolysis. The specificity for the desired form of native free Pyd or Dpd or both is supplied by the antibody preparation.

The immunoassays themselves are conducted using the variety of standard assay protocols generally known in the art. As is generally understood, the assay is constructed so as to rely on the interaction between the specific antibody and the desired analyte for specificity and to utilize some means to detect the complex formed by the analyte and the antibody. The complex formation may be between the antibody itself or an immunologically reactive fragment thereof such as an Fab, Fab', or F(ab')$_2$ fragments. The antibody or immunologically reactive fragment thereof may be complexed to solid support and used as a capture antibody for the analyte. This protocol may be run in a direct form, wherein the formation of analyte/antibody complex is detected by a fluorescent, radioactive or enzymatic label, or may be run in a competitive format wherein a labeled standard competes with analyte for the antibody. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous.

The antibodies and reagents for the conduct of an immunoassay using standard detection protocols—i.e., for example radioisotope labeling, fluorescent labeling or ELISA, either in a direct or competitive format can conveniently be supplied as kits which include the necessary components and instructions for the assay.

Since antibodies can be raised specifically to the forms of the native free crosslinks which comprise the various forms thereof, the ratios of these components can be determined as well as their individual levels and their total.

Thus, the assay can be designed to include antibodies or immunologically reactive fragments thereof which will result in determination of total native free crosslinks, or determination of native free Pyd, Dpd, Gal-Pyd, or Glc. Gal-Pyd, or any desired combination thereof. Since the levels of the Pyd and Dpd crosslinks in various tissues can be determined, alteration in their relative amounts can be used as an index for degradation of the particular tissue in question. For example, for most normal adults, the ratio of Pyd/Dpd stays constant throughout adulthood. As bone has a Pyd/Dpd ratio of 4/1 and appears to be the major source of liberated Dpd, an elevation in the ratio of Dpd/Pyd may be indicative of bone degradation. (Although aorta also contains Dpd, its turnover rate is low.) Assessment of the level of Dpd in biological fluids also yields a result which is relatively bone-specific. However, it appears that in many instances where a bone disorder is suspected, the total free crosslink level (Dpd+Pyd) can also be used as a measure when additional information is present. When the symptoms do not suggest a disease of cartilage such as rheumatoid arthritis, the majority of the excess crosslink in free form in biological fluids will be, in fact, due to the resorption of bone.

Since other connective tissues, such as cartilage, for the most part contain only Pyd, not Dpd, an elevation in the ratio of Pyd/Dpd may indicate diseases associated with such damage.

While immunoassays using the antibodies of the invention are convenient, the native free Pyd and Dpd crosslinks can also be determined in a variety of ways. Since the pyridinoline linkage is fluorescent, direct chromatography of the sample of biological fluid as described in the art can result in separation of Dpd from Pyd and of the glycosylated forms of Pyd and the intensity of the fluorescence of the peaks obtained provides an index to quantitation.

In the methods of the invention, therefore, the native free crosslinks can be determined either as a group or individually by determining the intensity of the fluorescence of the chromatographed material.

As set forth in PCT application WO89/04491 referenced above, the quantity of crosslinks can also be determined using specific electrodes of appropriate redox potential for the ring system.

In addition to the use of the native free cross-link as an indicator of bone resorption, bone metabolic balance is advantageously determined by combining this determination with the determination of a marker for formation of bone in the same or other appropriate biological fluid from the same individual. For example, such markers include procollagen type I, bone osteocalcin (also known as bone GLA protein or BGP); pro bone GLA protein, matrix GLA protein (MGP), bone specific proteins such as bone specific sialoprotein, phosphoproteins, alkaline phosphatase, osteonectin or other noncollagenous bone proteins. Methods for determination of these markers are well known in the art. Suitable methods for determination of these markers can be found, for example, in Delmas, P. D., et al., *J Bone Min Res* (1986) 1:333–337 (supra) for GLA.

The foregoing assays which provide an index to determination of the metabolic status of tissues which generate collagen-derived crosslinks when degradation occurs, are useful in a variety of contexts. First, they are a method to assess an abnormal condition of a subject by indicating, for example, excessive bone resorption. This may show, for example, the presence of an osteoporotic condition or the unfortunate metastatic progress of a malignancy. Other known conditions characterized by excessive bone resorption include Paget's disease and hyperparathyroidism. Since the condition of the subject can be monitored continuously, application of these assays can also be used to monitor the progress of therapy administered to treat these or other conditions. The assays can also be used as a measure of toxicity as the administration of toxic substances often results in tissue degradation.

Thus, the assays may be applied in any situation wherein the metabolic condition of collagen crosslink-containing tissues can be used as an index of the condition, treatment, or effect of substances directly administered to the subject or to which the subject is exposed in the environment.

The following examples are intended to illustrate but not to limit the invention.

EXAMPLE 1

Assay for Native Free Crosslinks in Urine

A. Isolation of U-Pyd and U-Dpd

Urine samples were collected from patients with Paget's disease or hyperparathyroidism (which contains elevated levels of free crosslinks) and from growing children (in which about 10-fold higher concentrations of crosslinks are present compared with normal adults). After concentration 10-fold by rotary evaporation, batches of the urine (20 liters) were subjected to partition chromatography batchwise on cellulose CF1 using butanol:acetic acid:water (4:1:1 v/v/v) as mobile phase. The pyridinium crosslink-containing fraction, eluted from the stationary phase with water, was chromatographed on a column (3.2×150 cm) of Sephadex G-10 eluted with 0.2M acetic acid. Pooled fractions containing the crosslinks were then made 67 mM in $Na^+$ and applied to a column (1.7×35 cm) of Dowex 50X-X8 ion-exchange resin equilibrated with 67 mM sodium citrate buffer, pH 2.75. After raising the column temperature to 60° C., elution with 67 mM sodium citrate was performed with a linear pH gradient from 2.75 to 5.50 over 500 ml. The column effluent was monitored by fluorescence (ex 325 nm/emm 400 nm) and the pooled fractions containing U-Pyd (364–377 ml) and U-Dpd (397–416 ml) were desalted by gel filtration on Sephadex G-10 and evaporated to dryness. The yield from 20 liters of urine was 2.5 µmoles U-Pyd and 0.6 µmoles U-Dpd.

B. Results

The isolation procedure set forth in paragraph A of this sample was applied to urine samples from individual patients and the amounts of U-Pyd and U-Dpd were quantitated using fluorescence measurements relative to creatinine as is known in the art (supra). The values obtained for normal individuals and in 7 patients with bone disorders and arthritic diseases are shown in Table 2. Values are given as the mean±SEM (n=6 in each group).

TABLE 2

| Patient Group | U-Pyd (nmol/mmol creatinine) | U-Dpd |
|---|---|---|
| Normal controls | 10.3 ± 1.0 | 3.27 ± 0.57 |
| Osteoporosis | 19.6 ± 2.3 | 5.90 ± 0.68 |
| Paget's disease | 62.5 ± 11.2 | 19.3 ± 3.83 |
| Hyperparathyroidism | 55.9 ± 14.2 | 16.3 ± 4.81 |
| Rheumatoid arthritis | 38.8 ± 8.36 | 8.92 ± 2.08 |
| Osteoarthritis | 25.8 ± 3.22 | 6.10 ± 0.83 |

These results show dramatically elevated levels of the free crosslinks in patients known to be suffering from diseases characterized by excessive breakdown of connective tissue.

Table 3 shows the proportions of U-Pyd and U-Dpd as a percentage of the total crosslink measured after hydrolysis in the different patient groups.

TABLE 3

| Patient Group | % U-Pyd* | % U-Dpd* |
|---|---|---|
| Normal controls | 43.8 ± 2.5 | 50.1 ± 5.4 |
| Osteoporosis | 41.7 ± 2.0 | 42.7 ± 2.6 |
| Paget's disease | 46.5 ± 2.4 | 47.4 ± 4.1 |
| Hyperparathyroidism | 48.7 ± 6.8 | 46.2 ± 6.9 |
| Rheumatoid arthritis | 38.1 ± 2.6 | 43.3 ± 1.8 |
| Osteoarthritis | 43.4 ± 3.9 | 47.0 ± 2.2 |

*Calculated as: (U-Pyd/total Pyd) × 100 and (U-Dpd/total Dpd) × 100. For all groups combined (n = 36), the correlation coefficient between U-Pyd and total Pyd was 0.929 (p < 0.0001) and between U-Dpd and total Dpd was 0.952 (p < 0.0001).

Since, as shown in Table 3, the percentage of U-Pyd and U-Dpd is relatively unchanged in patients with abnormal conditions as compared to controls, concentrations of the free crosslinks in urine reflect the same increase in collagen degradation in diseases compared with the controls as do the total crosslinks measured after hydrolysis of the urine.

U-Pyd and U-Dpd therefore provide viable indices of collagen degradation to facilitate diagnosis and monitoring of diseases involving abnormalities of connective tissue metabolism.

C. Immunoassay

Native free Crosslinks isolated by the method described in paragraph A of this example are used for the preparation of antigen. U-Pyd and U-Dpd are further purified by ion-exchange chromatography with 67 mM-sodium citrate buffer, pH 4.25 using a high-resolution resin column of an amino acid analyzer (Locarte Co. Ltd., London, UK).

For immunization, the isolated crosslinks are covalently attached to bovine serum albumin using carbodiimide reagents and methods well known in the art.

Both monoclonal and polyclonal antibodies are raised against the urinary crosslink components. For the production of monoclonal antibodies, Balb/c mice are immunized with urinary crosslink-BSA conjugates, and hybridoma cell lines are prepared using standard techniques after fusions of cells from the spleen or lymph nodes with Ag8 myeloma cells. Polyclonal antibodies are raised in rabbits. Screening of both antisera and hybridoma cell media is performed by ELISA using microtiter plates coated with the appropriate urinary crosslink-gelatin conjugate prepared as described by Robins, Biochem J (1982) 217:617–620.

Assays for each of the crosslink components present in free form in urine are performed by an inhibition ELISA as follows:

Urine samples (5 or 20 μl) or solutions containing 0.2–20 pmol of purified urinary crosslink reference standard are diluted to 110 μl with phosphate buffered saline containing 0.05% Tween-20 detergent (PBS-T), and are added to 110 μl of primary antibody, immunoreactive fragment, or antiserum diluted 1:5,000–1:20,000 in PBS-T. Each sample is prepared in triplicate in round-bottomed, 96-well microtiter plates which are then incubated overnight at room temperature.

Portions (200 μl) of the samples are transferred to flat-bottomed microtiter plates previously coated with gelatine conjugate containing the appropriate urinary crosslink component. After 30 minutes, the plate is washed with PBS-T (3 times) and the bound antibodies detected by standard techniques with a biotin-labeled antibody prepared against the species of the primary antibody combined with a streptavidin-peroxidase and peroxidase substrate detection system. Color development is measured at 492 nm using an automated microtiter plate reader. Samples containing the analyte decrease the binding of primary antibody to the plate and thus have reduced color concentration. The amount of free crosslinks in the sample is quantified with reference to curves from standards included on each plate computed using log-log plots.

The foregoing assay can be reformatted to be conducted directly by coating the sample suspected of containing antigen in the flat-bottom microtiter plate, and adding labeled primary antibody directly to the wells. After washing, the amount of labeled antibody remaining in the testing solution is determined. A decrease in levels indicates the presence of antigen.

EXAMPLE 2

Sources of Native Free Crosslink

In order to determine a source for native free crosslinks usable as standards in the assays of the invention, the urine of a number of species of large animals was analyzed. In bovine urine, the Pyd/Dpd ratio is 12±2 with only about 15% as free crosslink; the values in sheep are similar except for only about 20–25% is free crosslink. In pig urine, the ratio of Pyd/Dpd is about 5±1 and the proportion of free crosslink relative to total is 42±5%. The concentrations of free crosslinks are about 380 nM for Pyd and 70 nM for Dpd.

Children's urine appears to give a better yield of Dpd than urine from adults. Some preferential loss of Dpd from pig urine occurs when CF-1 cellulose is used in the purification procedure, and overall recovery of Pyd is 40–50% for Pyd but only 20% for U-Dpd. Using children's urine as a starting material, recovery for both crosslinks is about 55%.

Accordingly, both children's and pig urine are suitable sources for free crosslink standards.

As set forth above, the yield of crosslink in the diastereomeric form characteristic of native free crosslink could be improved by liberating total crosslinks in these sources by enzymatic hydrolysis procedures, such as the use of exopeptidases and glycosidases.

EXAMPLE 3

Pyd/Dpd in Human Tissues

Analyses of a range of different tissues has shown that the crosslink content of cortical bone is slightly higher than that of trabecular bone with a Pyd/Dpd ratio of about 4.2. Although Dpd was not detected in cartilage, this crosslink was present in aorta and in ligaments. These results are summarized in Table 4.

TABLE 4

| Tissue | n | Pyd (residues/molecule) | Dpd |
|---|---|---|---|
| Articular cartilage | 15 | 1.47 ± 0.23 | N.D. |
| Cortical bone | 15 | 0.35 ± 0.09 | 0.08 ± 0.02 |
| Trabecular bone | 7 | 0.26 ± 0.08 | 0.06 ± 0.02 |
| Aorta | 14 | 0.30 ± 0.07 | 0.07 ± 0.01 |
| Invertebral disc | 25 | 1.14 ± 0.11 | N.D. |
| Ligaments | 10 | 0.47 ± 0.35 | 0.05 ± 0.03 |

Both Pyd and Dpd are completely absent from the collagens of normal skin, nor are they present in immature or newly synthesized collagens.

EXAMPLE 4

Determination of Free Crosslinks in Osteoporosis Patient Urine

Sixty-four postmenopausal women with vertebral fractures (type I osteoporosis) aged 53 to 74 years (mean±SD, 64±5 years) were studied. All women had lumbar spin bone mineral density below the fracture threshold of 0.98 g/cm$^2$ as measured by dual-photon absorptiometry and spine radiographs showing three or more grade i fractures or one or more grade 2 fractures. No other secondary cause for the osteoporosis was identified.

As a control group, 67 postmenopausal women with mean (±SD) age of 65±6 years (range 50 to 79 years) were studied. All women had normal spin radiographs and had lumbar spine bone mineral densities within the normal range for age as measured by dual-photon absorptiometry. None had any illness or were taking drugs known to affect bone metabolism.

For measurements of hydroxyproline, the subjects were maintained on a gelatin-free diet for three days prior to the study. Urine samples were collected and aliquots were stored at −70° C. until analyzed. The total crosslinks were measured essentially as described previously (Black, D., et al., Anal Biochem (1988) 169:197–203; Seibel, M. J., et al., J Rheumatol (1989) 16:964–970). For the determination of U-Pyd and U-Dpd in unhydrolyzed urine, 0.5 ml portions were processed directly by partition chromatography on CF1 cellulose (which separates the free from peptide-derivatized forms prior to the HPLC step; HPLC was conducted as for the hydrolyzed samples). Hydroxyproline in acid hydrolysates of urine was measured by HPLC (Dawson, C., et al., Clin Chem (1988) 34:1572–1574).

Measurements of native free pyridinium crosslinks and of total hydroxyproline in urine for the control and osteoporotic groups are shown in Table 5. The results showed that the excretion of the bone-specific crosslink, U-Dpd, was significantly higher in the osteoporotic group compared with the controls.

TABLE 5

| | Osteoporotic | | Controls | |
|---|---|---|---|---|
| | nmol/mmol creatinine | nmol/24 h creatinine | nmol/mmol | nmol/ 24 h |
| U-Pyd | 21.4 ± 6.6** | 170 ± 47 | 18.4 ± 5.8 | 151 ± 49 |
| U-Dpd | 5.7 ± 2.0*** | 45 ± 14*** | 4.6 ± 1.7 | 37 ± 13 |
| U-Pyd.Gal.Glc | 5.2 ± 2.1 | 41 ± 15 | 4.6 ± 2.0 | 38 ± 16 |
| Hydroxyproline (×10$^{-3}$) | 21.4 ± 7.4** | 175 ± 66 | 18.2 ± 6.7 | 156 ± 77 |

Statistical significance (Student's t-test) of the difference compared with the corresponding control group is shown:
*p < 0.05; p < 0.01; *p < 0.001

Differences were less marked for U-Pyd; the values for the glycosylated derivative, U-Pyd, Gal, Glc, were not statistically different. Linear regression analysis showed that there were highly significant correlations between values expressed as creatinine ratios and as the total 24 h excretion for both U-Pyd (r=0.80) and U-Dpd (r=0.82). This observation is consistent with the finding that there were no significant variations diurnally in crosslink excretion for healthy male or female volunteers (A. M. McLaren and S. P. Robins, unpublished results).

There were significant correlations of U-Dpd with hydroxyproline which were more marked in the osteoporotic group (r=0.53; p<0.001) than in the controls (r=0.21; N.S.). The relationship between U-Pyd and hydroxyproline was similar with correlation coefficients for the osteoporotic and control groups of r=0.45 (p<0.001) and r=0.34 (p<0.01), respectively.

For samples where both free and total crosslinks were measured, there were highly significant correlations between these values. For deoxypyridinoline, the correlation coefficients for the osteoporotic group (n=25) and control group (n=24) were 0.90 and 0.84, respectively; the corresponding correlations for pyridinoline were r=0.96 and r=0.85.

I claim:

1. A method of screening for or monitoring a bone resorption disorder in a human subject, comprising,
obtaining a non-hydrolyzed urine sample from the subject,
determining a ratio of native peptide-free, non-glycosylated pyridinoline (N-Pyd)/creatinine, peptide-free deoxypyridinoline (N-Dpd)/creatinine, or both, in the sample, and
comparing the ratio determined with the same ratio for normal subjects, where an elevated ratio provides an indication that the test subject has an above-normal rate of bone resorption.

2. The method of claim 1, wherein the ratio determined is N-Pyd/creatinine.

3. The method of claim 1, wherein the ratio determined is N-Dpd/creatinine.

4. A method of screening for or monitoring a bone resorption disorder related to osteoporosis, hyperparathyroidism, rheumatoid arthritis, osteoarthritis, a malignant tumor or metastatic cancer in bone, or Paget's disease in a human subject, comprising,
obtaining a non-hydrolyzed urine sample from the subject,
determining a ratio of native peptide-free, non-glycosylated pyridinoline (N-Pyd)/creatinine, peptide-free deoxypyridinoline (N-Dpd)/creatinine, or both, in the sample, and
comparing the ratio determined with the same ratio for normal subjects, where an elevated ratio provides an indication that the test subject may have one of the bone-resorption disorders.

5. The method of claim 4, wherein the ratio determined is N-Pyd/creatinine.

6. The method of claim 4, wherein the ratio determined is N-Dpd/creatinine.

7. The method of claim 4, wherein the bone resorption disorder relates to osteoporosis.

8. The method of claim 4, wherein the bone resorption disorder relates to hyperparathyroidism.

9. The method of claim 4, wherein the bone resorption disorder relates to rheumatoid arthritis.

10. The method of claim 4, wherein the bone resorption disorder relates to osteoarthritis.

11. The method of claim 4, wherein the bone resorption disorder relates to a malignant tumor or metastatic cancer in bone.

12. The method of claim 4, wherein the bone resorption disorder relates to Paget's disease.

13. The method of claim 4, for screening for such a bone resorption disorder.

* * * * *